(12) United States Patent
Hu et al.

(10) Patent No.: US 8,208,137 B2
(45) Date of Patent: Jun. 26, 2012

(54) MOLECULE DETECTION USING RAMAN LIGHT DETECTION

(75) Inventors: Min Hu, Sunnyvale, CA (US); Alexandre M. Bratkovski, Mountain View, CA (US); Jingjing Li, Palo Alto, CA (US); Huei Pei Kuo, Cupertino, CA (US); Zhiyong Li, Redwood City, CA (US); Fung Suong Ou, Palo Alto, CA (US); Michael Josef Stuke, Palo Alto, CA (US); Michael Renne Ty Tan, Menlo Park, CA (US); Shih-Yuan Wang, Palo Alto, CA (US); Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 356 days.

(21) Appl. No.: 12/696,853

(22) Filed: Jan. 29, 2010

(65) Prior Publication Data
US 2011/0188033 A1 Aug. 4, 2011

(51) Int. Cl.
*G01J 3/44* (2006.01)
(52) U.S. Cl. ...................................................... 356/301
(58) Field of Classification Search .................... 356/301
See application file for complete search history.

(56) References Cited

U.S. PATENT DOCUMENTS

| | | | |
|---|---|---|---|
| 4,505,586 A | 3/1985 | Tochigi et al. | |
| 6,002,471 A | 12/1999 | Quake | |
| 6,989,897 B2 | 1/2006 | Chan et al. | |
| 7,151,598 B2 * | 12/2006 | Poponin | 356/301 |
| 7,528,948 B2 * | 5/2009 | Bratkovski et al. | 356/301 |
| 7,609,377 B2 * | 10/2009 | Wu et al. | 356/301 |
| 7,692,785 B2 * | 4/2010 | Sutherland et al. | 356/301 |
| 7,847,933 B2 * | 12/2010 | Malinovskaya et al. | 356/301 |

* cited by examiner

*Primary Examiner* — Layla Lauchman

(57) ABSTRACT

An apparatus for detecting at least one molecule using Raman light detection includes a substrate for supporting a sample containing the at least one molecule, a laser source for emitting a laser beam to cause Raman light emission from the at least one molecule, a modulating element for modulating a spatial relationship between the laser beam and the substrate at an identified frequency to cause the Raman light to be emitted from the at least one molecule at the identified frequency, at least one detector for detecting the Raman light emitted from the at least one molecule, and a post-signal processing unit configured to process the detected Raman light emission at the identified frequency to detect the at least one molecule.

20 Claims, 8 Drawing Sheets

MOLECULE DETECTION USING RAMAN LIGHT DETECTION

GOVERNMENT LICENSE RIGHTS

The U.S. Government has a paid-up license in this invention and the right in limited circumstances to require the patent owner to license others on reasonable terms as provided for by the terms of (Contract number HR0011-09-3-0002) awarded by the Defense Advanced Research Projects Agency.

BACKGROUND

Raman spectroscopy has been utilized for a number of years to identify single molecules from various types of samples. Raman spectroscopy, more particularly, has been utilized to identify the vibrational modes of molecules to distinguish between different molecular species. The probability, however, of a Raman interaction occurring between an excitatory beam of light and an individual molecule in a sample is very low, for instance, $10^{30}$ cm$^2$ for CN. As such, the use of Raman spectroscopy to identify individual molecules has been relatively limited.

One approach to enhancing the Raman spectroscopy effect is to place the molecules near roughened silver surfaces. The surface enhanced Raman spectroscopy (SERS) effect is related to the phenomenon of plasmon resonance, in which metal nanoparticles exhibit an increased optical resonance in response to incident electromagnetic radiation, due to the collective coupling of conduction electrons in the metal. Attempts at implementing SERS have included coating metal nanoparticles or fabricating rough metal films on the surface of the substrate and then applying a sample to the metal-coated surface.

BRIEF DESCRIPTION OF THE DRAWINGS

Embodiments are illustrated by way of example and not limited in the following figure(s), in which like numerals indicate like elements, in which.

DETAILED DESCRIPTION

For simplicity and illustrative purposes, the principles of the embodiments are described by referring mainly to examples thereof. In the following description, numerous specific details are set forth in order to provide a thorough understanding of the embodiments. It will be apparent however, to one of ordinary skill in the art, that the embodiments may be practiced without limitation to these specific details. In other instances, well known methods and structures are not described in detail so as not to unnecessarily obscure the description of the embodiments.

Disclosed herein is an apparatus for detecting at least one molecule in a sample with a relatively high level of precision through improved processing of Raman light emissions from the at least one molecule. The accuracy of the molecule detection is relatively high because the apparatus disclosed herein significantly increases the signal-to-noise ratio in the processing of the Raman light emissions. As discussed in greater detail herein below, a spatial relationship between a laser beam that causes the molecule to emit Raman light and a substrate on which the molecule is supported is modulated at an identified frequency. In addition, a post-signal processing unit is configured to process the detected Raman light emitted from the molecule at the identified frequency. In one regard, the post-signal processing unit or a computing device is configured to lock into the identified frequency and to filter out signals in other frequencies when processing the detected Raman light, which results in the increased signal-to-noise ratio.

According to an embodiment, the apparatus disclosed herein is implemented to modulate a spatial relationship between the laser beam and the substrate to cause the laser beam to illuminate multiple molecules during a single modulation cycle. The apparatus is also configured to concurrently detect and process the Raman light emitted by the multiple molecules.

According to another embodiment, the apparatus disclosed herein is implemented to determine the locations of one or more molecules with respect to a substrate. In this embodiment, the apparatus is configured to detect the intensity levels of the Raman light emitted by the one or more molecules as the spatial relationship between the laser beam and the substrate is modulated. In addition, the intensity levels may be evaluated to determine which location along one or more dimensions of the substrate resulted in the substantially highest intensity level and that location may be determined as the location of the molecule.

Figure 1:
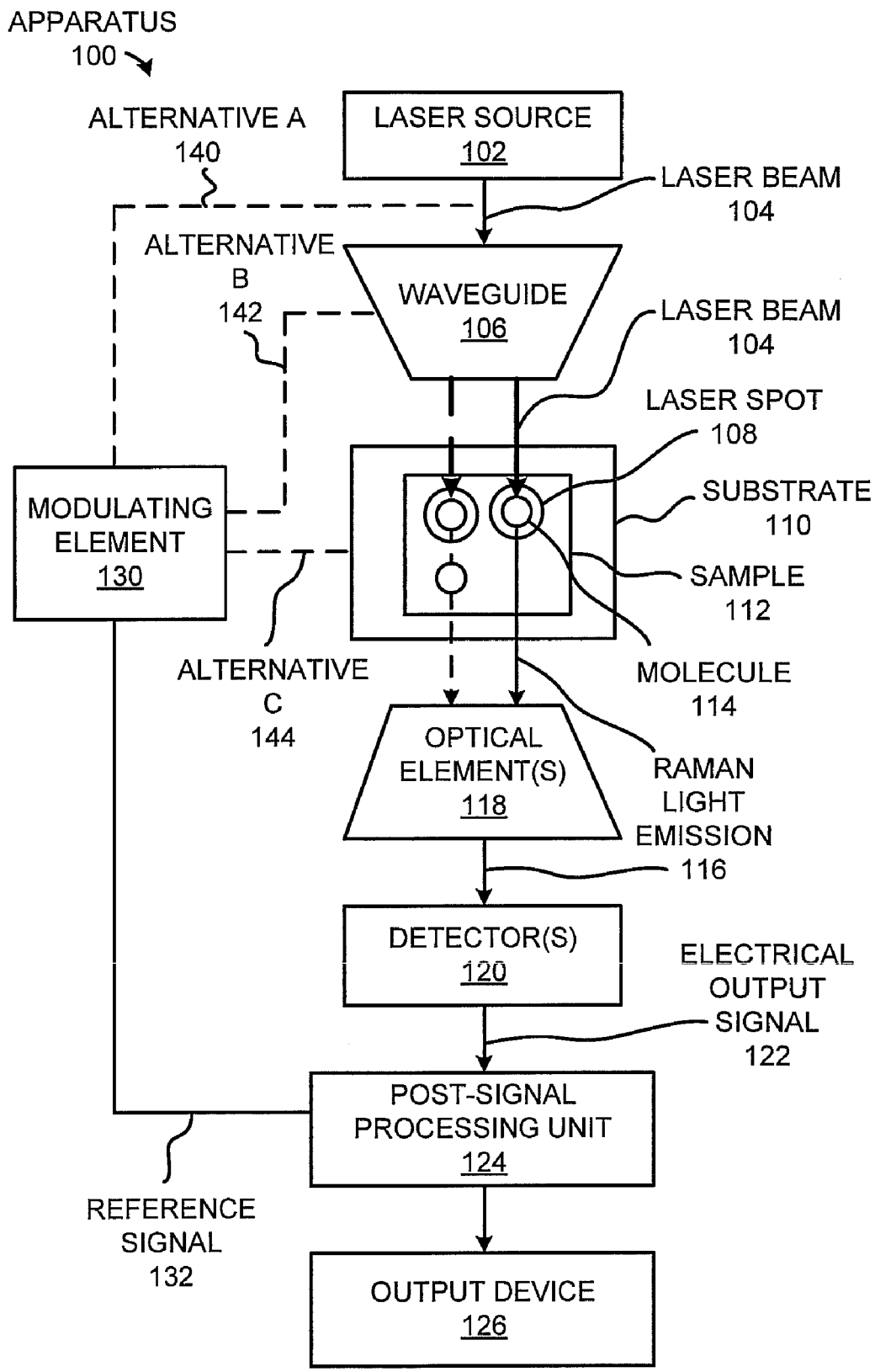
FIG. 1 a simplified schematic diagram of an apparatus for detecting at least one molecule in a sample using Raman light detection, according to an embodiment of the invention.

With reference first to FIG. 1, there is shown a simplified schematic diagram of an apparatus 100 for detecting at least one molecule in a sample using Raman light detection, according to an embodiment. It should be understood that the apparatus 100 depicted in FIG. 1 may include additional components and that some of the components described herein may be removed and/or modified without departing from a scope of the apparatus 100. It should also be understood that the components depicted in FIG. 1 are not drawn to scale and thus, the components may have different relative sizes with respect to each other than as shown therein.

As shown, the apparatus 100 includes a laser source 102 configured to continuously emit a laser beam 104, which may have, for instance, a wavelength of around 400-600 nm. The laser beam 104 is transmitted through a waveguide 106, such as an optical fiber, prior to irradiating a sample 112 of one or more molecules 114 contained on a substrate 110. Although not explicitly shown, the laser beam 104 may traverse an optical path containing one or more optical devices configured to manipulate, for instance, the direction, intensity, etc., of the laser beam 104.

As further shown in FIG. 1, the laser beam 104 is configured to illuminate a molecule 114 and cause a Raman effect on the molecule 114 and thereby cause Raman light to be emitted or scattered from the molecule 114. The Raman light emitted 116 from the molecule 114 is collected by one or more optical elements 118. The optical elements 118 may include, for instance, a condenser lens system, a spectrometer, a filter, etc. For instance, the emitted Raman light 116 is focused by the condenser lens system and undergoes wavelength dispersion in the spectrometer prior to reaching one or more optical detectors 120 to, for instance, convert the emitted Raman light 116 to a monochromated light. The optical detector(s) 120 receives the emitted Raman light 116 and converts it to an electrical output signal 122, which is transmitted to a post-signal processing unit 124. Although not shown, the electrical output signal 122 may be amplified prior to or during transmission to the post-signal processing unit 124.

The components of the apparatus 100 may be arranged in any suitable manner. For instance, the optical elements 118 and the detector(s) 120 may be arranged on the same side of the molecule 114 as the as laser beam 104. In another example, the substrate 110 may comprise a transparent substrate, such as glass, and the optical elements 118 and the detector(s) 120 may be arranged to capture Raman light 116 that is emitted through the substrate 110.

Also depicted in FIG. 1 is a modulating element 130 for modulating a spatial relationship between the laser beam 104 and the substrate 110. The modulating element 130 may be configured to modulate the spatial relationship between the laser beam 104 and the substrate 110 at an identified frequency to cause the Raman light 116 to be emitted from the molecule 114 at the identified frequency. In one example, the amplitude of the modulation is selected to enable the laser beam 104 to intermittently irradiate the molecule 114 during a modulation cycle. Thus, in an example in which the laser beam 104 has a diameter of $1\lambda$, the amplitude of the modulation is set to be at least $1\lambda$.

As discussed in greater detail herein below, the modulating element 130 is configured to modulate either or both the spatial position of the laser beam 104 and the substrate 110 to effectuate the spatial relationship modulation between the laser beam 104 and the substrate 110. In any regard, the post-signal processing unit 124 is configured to process the detected Raman light emission 116 at the identified frequency to, for instance, determine the species of the molecule 114.

In one regard, the post-signal processing unit 124 is configured to implement a lock-in detection technique on the detected Raman light emission 116 at the identified frequency. As such, for instance, the post-signal processing unit 124 includes a lock-in amplifier, a boxcar amplifier, or the like, which serves to detect and amplify only the signal component of the electrical output signal 122 from the detector(s) 120 that has the same frequency as that of the identified frequency at which the modulating element 130 modulates the either or both of the laser beam 104 and the substrate 110. Because the post-signal processing unit 124 detects and amplifies only the signal component of the electrical output signal 122 that has the same frequency as that of the identified frequency of a reference signal 132 received from the modulating element 130, the input signal component having a frequency different from that of the reference signal 132 is not sampled. Further, by selecting appropriately the locked-in phase, the post-signal processing unit 124 may sample the signal component ascribable to a particular molecule 114.

Figure 2A:
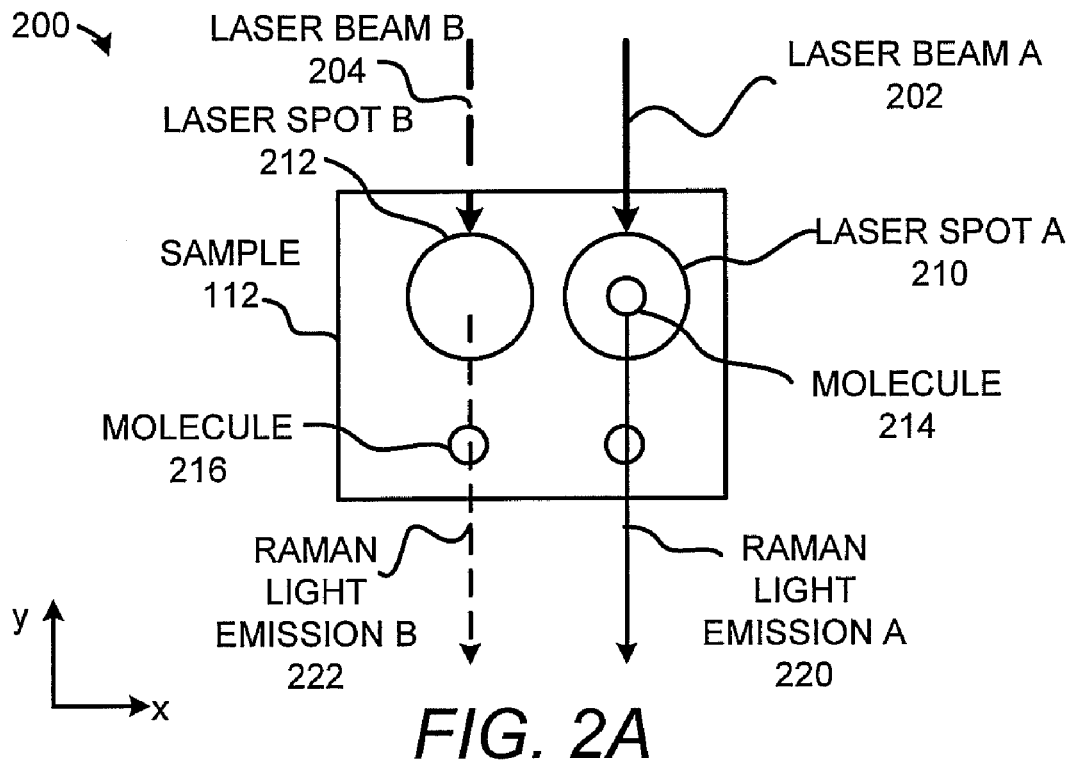
FIGS. 2A and 2B, respectively, illustrate simplified and enlarged schematic diagrams of the sample depicted in FIG. 1, according to embodiments of the invention.

With reference now to FIG. 2A, there is shown a simplified and enlarged schematic diagram 200 of the sample 112 depicted in FIG. 1, according to an embodiment. The diagram 200 generally depicts a manner in which the spatial relationship between the laser beam 104 and the substrate 110 is modulated. As shown therein, the spatial relationship between the laser beam 104 and the substrate 110 is configured to modulate between a first position "A" and a second position "B". More particularly, the first position "A" results in a laser beam A 202 irradiating a first laser spot A 210 and the second position "B" results in the laser beam B 204 irradiating a second laser spot B 212. In the example depicted in FIG. 2A, the first position A on the sample 112 contains a molecule 214, but the second position B does not contain a molecule of interest. Thus, for instance, another molecule of the sample 112 or the substrate 110 other than a molecule of interest may be contained at the second position B.

When the laser spot A 210 irradiates the first position A, the molecule 214 emits a first Raman light A 220 that is processed as discussed above with respect to FIG. 1. Likewise, when the laser spot B 212 irradiates the second position B, a Raman light B 222 is emitted from a substance that is not a molecule of interest. The emitted Raman light B 222 is also processed as discussed above. In this embodiment, the Raman light B 222 emitted from a location that does not contain a molecule of interest is processed to determine a background noise level of the sample 112 or the substrate 110. In addition, the post-signal processing unit 124 or other processing device, such as a computer device, may utilize the determined background noise level in improving the signal-to-noise ratio of the signal received from the Raman light emitted 220 from the molecule 214.

According to another embodiment, the apparatus 100 is implemented to concurrently detect multiple molecules as the spatial relationship between the laser beam 104 and the substrate 110 is modulated. In this embodiment, and with particular reference to the diagram 250 in FIG. 2B, a molecule 216 of interest is located at the second location B. In addition, the molecule 216 emits a Raman light B 222 when the laser spot 212 is in the second location B. Moreover, the post-signal processing unit 124 or other processing device, such as a computer device, may parallel process the Raman light emissions 220 and 222 received from the molecules 214 and 216, for instance, to detect the molecular species of both of the molecules 214 and 216.

Figure 2B:
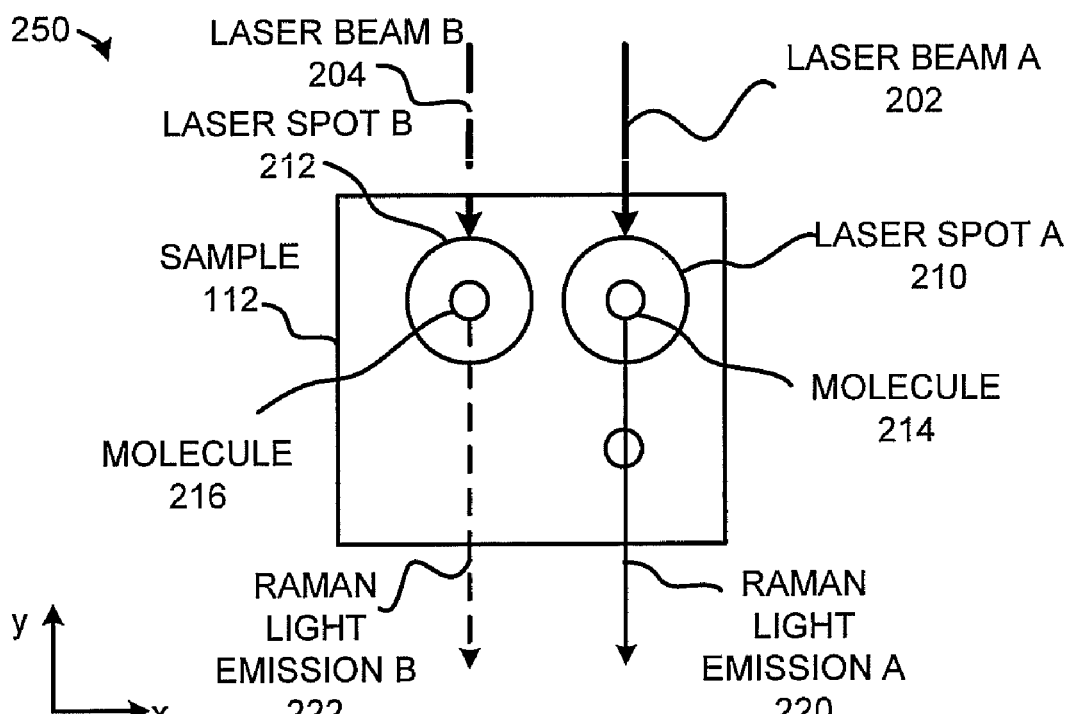

In the embodiments depicted in FIGS. 2A and 2B, although the laser spots 210 and 212 have been discussed as moving along a single dimension, it should be understood that the spatial relationship of the laser beam 104 and the substrate 110 may instead be modulated along multiple dimensions. For instance, the spatial relationship may be modulated in both the x and y directions to enable the laser beam 104 to illuminate more than two molecules 114 during a single modulation cycle.

Figure 3:
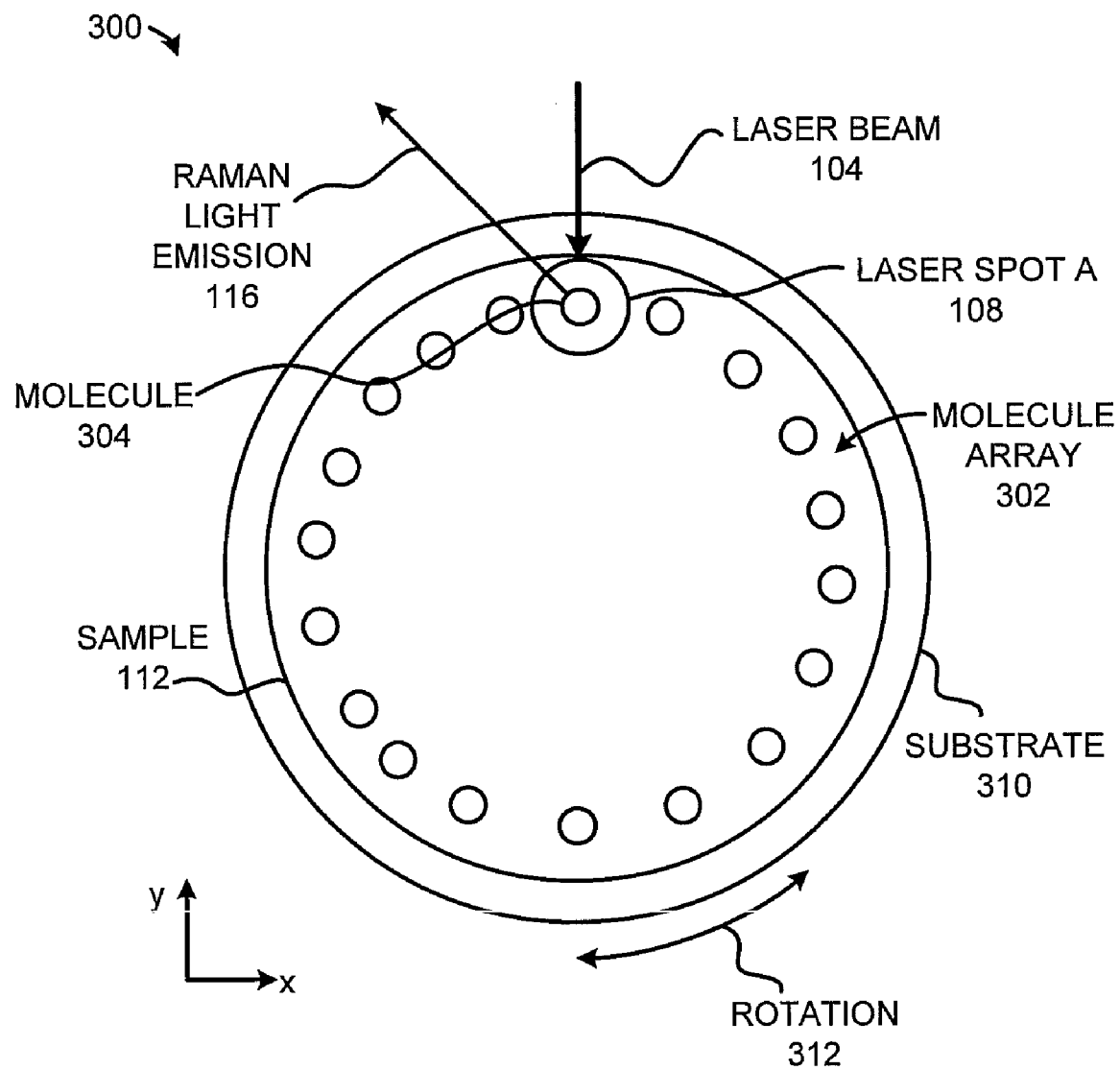
FIG. 3 illustrates a simplified schematic diagram of an array of molecules disposed around a circular substrate, according to an embodiment of the invention.

By way of particular example, and with reference to FIG. 3, there is shown a simplified schematic diagram 300 of an array of molecules 302 disposed around a circular substrate 310. As shown therein, at a first time, the laser beam 104 forms a laser spot 108 on one of the molecules 304 causing a Raman light 116 to be emitted therefrom. At a second time, either or both of the substrate 310 and the laser beam 104 is modulated (as indicated by the arrow 312) to cause the laser spot 108 to irradiate another molecule 304 of the array 302 or a location that does not contain a molecule of interest. At the second time, another Raman light 116 is emitted from the another molecule 304 or another substance. This process may be continuously repeated as the relative spatial position of the laser beam 104 with respect to the substrate 310 is continuously modulated.

The relative spatial position of the laser beam 104 with respect to the substrate 310 in FIG. 3 is modulated at an identified frequency. In addition, the post-signal processing unit 124 (FIG. 1) is configured to process the detected Raman light emissions 116 from the molecules 304 and in certain embodiments, the detected Raman light emissions 116 from other substances, as discussed above. As such, the post-signal processing unit 124 may be configured to continuously and concurrently process multiple molecules.

With reference back to FIG. 1, the modulating element 130 is depicted as having multiple alternatives for modulating the spatial relationship between the laser beam 104 and the substrate 110 at an identified frequency (as noted by the dashed and full arrows between the waveguide 106 and the optical elements 118). In a first alternative 140, the modulating element 130 comprises an electro-optic deflector configured to modulate the spatial position of the laser beam 104 at the identified frequency along one or more dimensions to thereby modulate the position of the laser spot 108 with respect to the substrate 110. In a second alternative 142, the modulating element 130 is configured to modulate the spatial position of the optical waveguide 106 to thereby modulate the position of the laser spot 108. In a third alternative 144, the modulating element 130 is configured to modulate the spatial position of the substrate 110 with respect to the laser beam 104 to thereby modulate the spatial position of the laser spot 104 with respect to the substrate 110.

In the second and third alternatives 142 and 144, the modulating element 130 may comprise any suitable mechanical device configured to modulate either or both of the optical waveguide 106 and the substrate 110. Examples of suitable mechanical devices include MEMS devices, piezoelectric devices, a voice coil, etc.

Figure 4A:
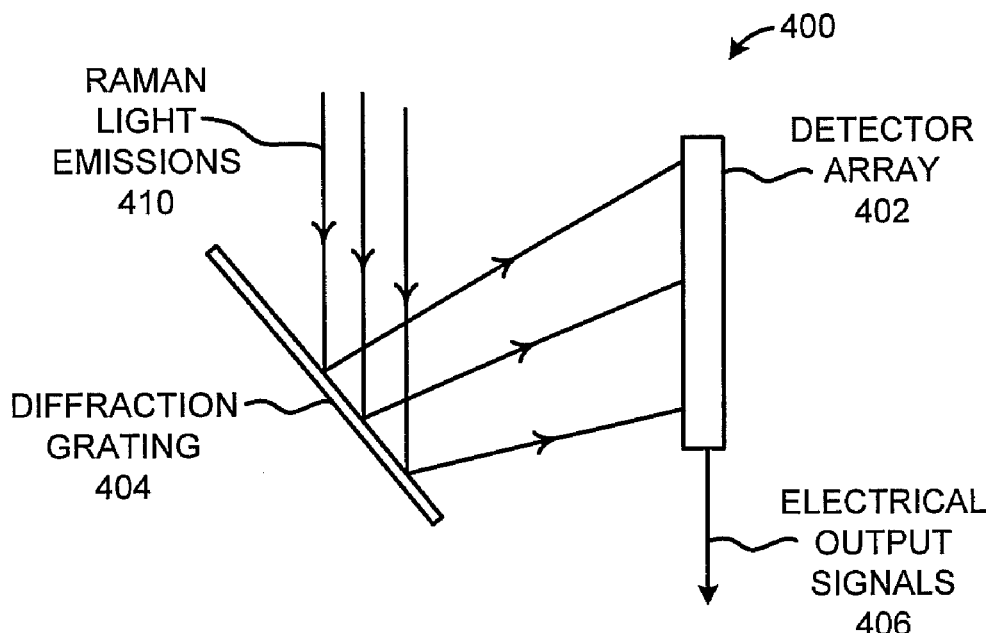
FIGS. 4A and 4B, respectively, illustrate simplified and enlarged diagrams of the detector(s) depicted in FIG. 1 formed of an array of detectors, according to embodiments of the invention.

According to another embodiment, the one or more detectors 120 comprise at least one wide area detector configured to detect the laser spots 108 at multiple displacements. In addition or alternatively, and with particular reference to FIG. 4A, there is shown a simplified and enlarged diagram 400 of the detector(s) 120 formed of an array of detectors 402, according to an embodiment. The array of detectors 402 may be formed of a plurality of detectors, in which each of the detectors is configured to detect light received from a different location with respect to the substrate 110. Also shown therein is a diffraction grating 404 which splits and diffracts the Raman light emissions 410 into several beams that travel into different directions and onto the deflectors of the detector array 402. Moreover, the detectors in the detector array 402 are configured to send electrical output signals 406 to the post-signal processing unit 124 as discussed above with respect to the detector(s) 120 in FIG. 1.

Figure 4B:
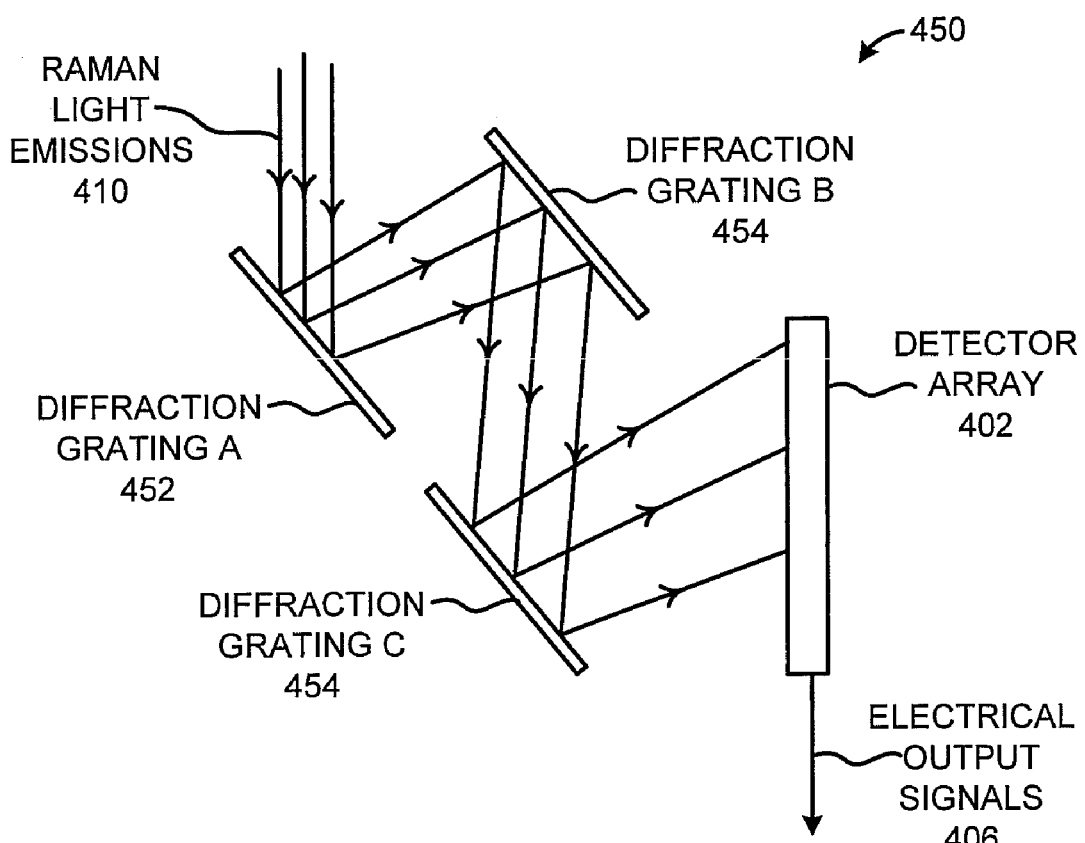

Turning now to FIG. 4B, there is shown a simplified and enlarged diagram 450 of the detector(s) 120 formed of an array of detectors 402, according to another embodiment. As shown therein, instead of being diffracted by a single diffraction grating 404 as in the diagram 400, in the diagram 450, the Raman light emissions 410 are diffracted by multiple diffraction gratings 452-456 prior to reaching the detector array 402. The multiple diffraction gratings 452-456 generally operate to increase the spacing between the Raman light emissions 410 to thus enable relatively larger detectors in the detector array 402 to be implemented in detecting the Raman light emissions 410 from multiple locations on the substrate 110. The detectors in the detector array 402 are also depicted as being configured to send electrical output signals 406 to the post-signal processing unit 124 as discussed above with respect to the detector(s) 120 in FIG. 1.

Figure 5:
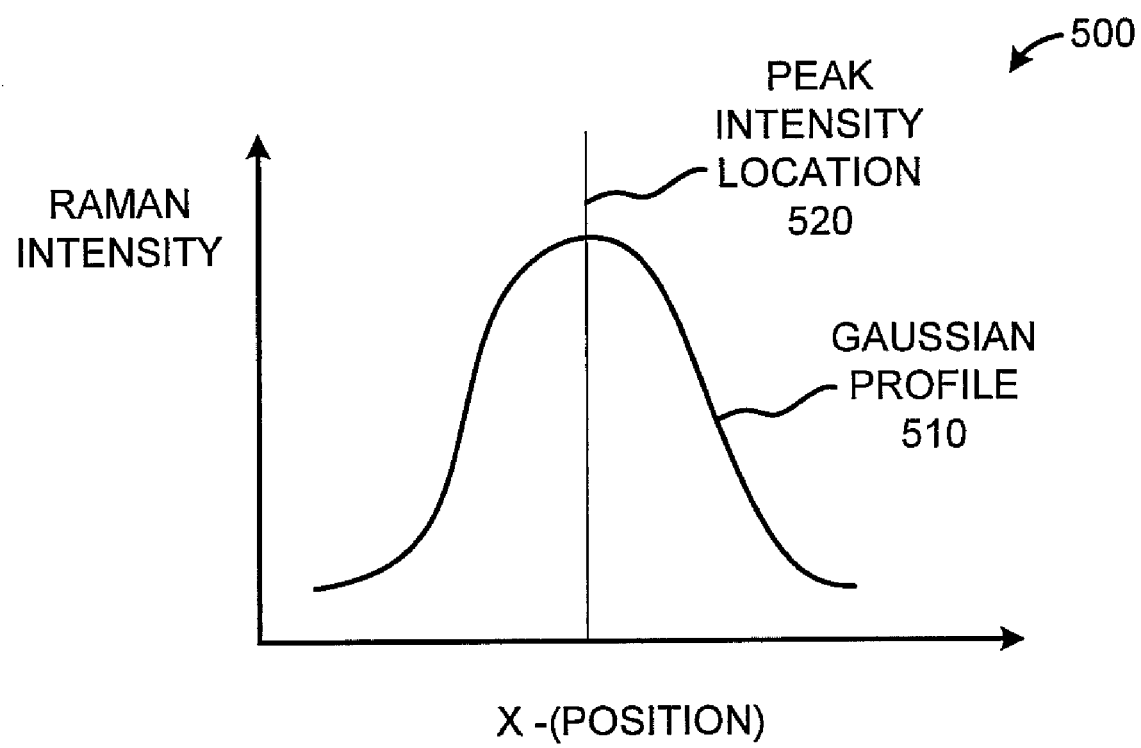
FIG. 5 illustrates a simplified schematic diagram depicting a relationship between Raman light intensity and position along a substrate, according to an embodiment of the invention.

According to another embodiment, the post-signal processing unit 124 or other computing device is configured to determine a location of at least one molecule 114 based upon intensities of the detected Raman light emissions 116 detected at different spatial relationships between the laser beam 104 and the substrate 110. More particularly, for instance, and with reference to FIG. 5, the intensities of the Raman light emissions 116 may be tracked with respect to various positions of the substrate 110. As shown in FIG. 5, the location of the molecule 114 is depicted as being determined along an X-axis (x-position), but it should be understood that similar techniques may be implemented to determine the location of the molecule 114 along a Y-axis (y-position) to thereby determine a two-dimensional location of the molecule 114.

As shown in the diagram 500 of FIG. 5, the intensity of the Raman light emission varies depending upon which location of the substrate 110 is irradiated by a laser spot 108. Thus, by tracking the intensities of the Raman light emissions 116 with respect to the substrate 110, a Gaussian profile 510 may be developed and a location on the Gaussian profile 510 where the intensity level peaks 520 may be determined. This location of the intensity level peak 520 may be translated into a particular location in either one or two dimensions with respect to the substrate 110. In one regard, the identified locations of one or more molecules 114 may be employed to more accurately position the laser beam 104 onto the one or more molecules 114 during a determination operation of the one or more molecules 114.

Figure 6:
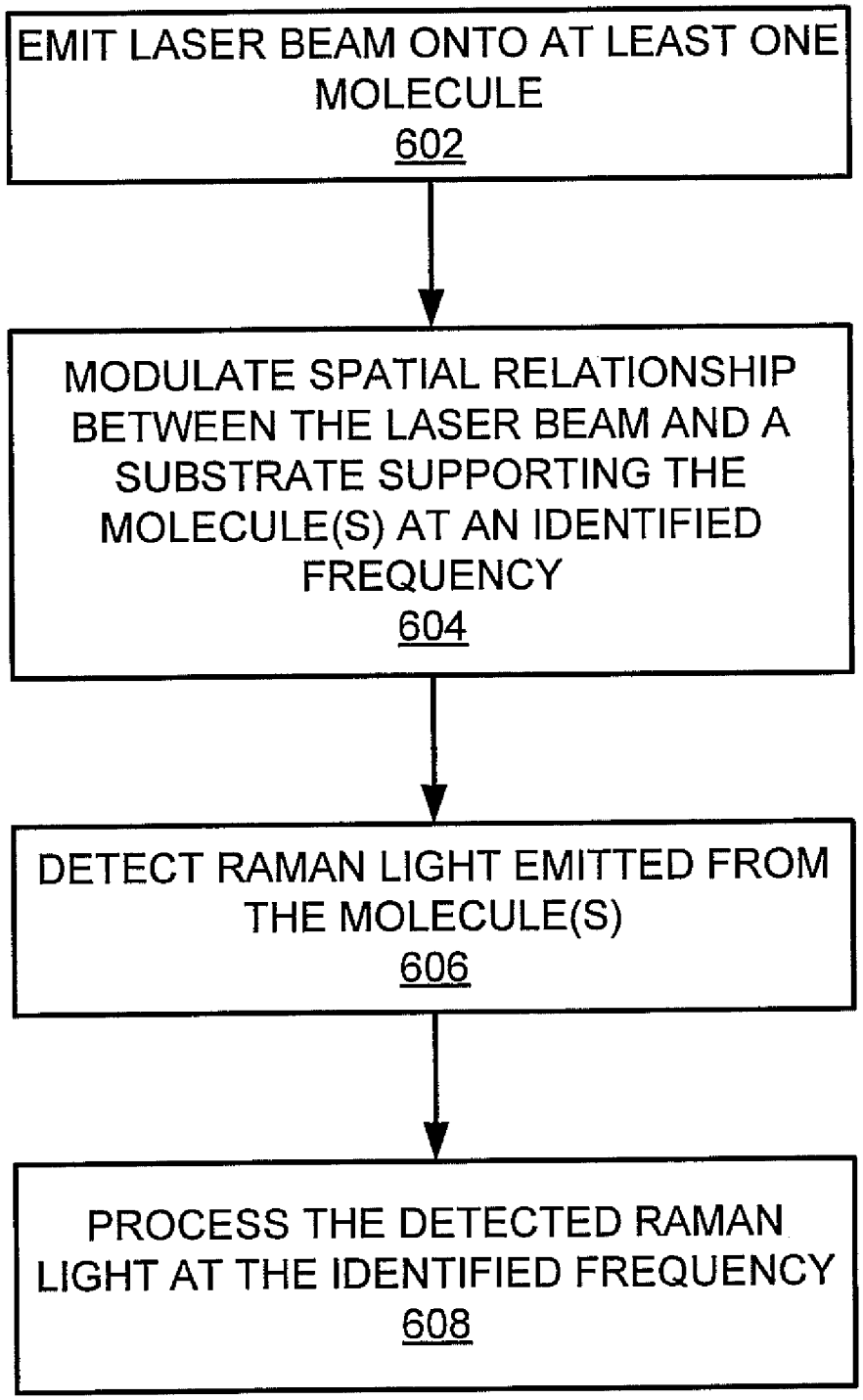
FIG. 6 shows a flow diagram of a method for detecting at least one molecule supported on a substrate using Raman light detection, according to an embodiment of the invention

Turning now to FIG. 6, there is shown a flow diagram of a method 600 for detecting at least one molecule 114 supported on a substrate 110 using Raman light detection, according to an embodiment. It should be understood that the method 600 depicted in FIG. 6 may include additional steps and that some of the steps described herein may be removed and/or modified without departing from a scope of the method 600.

At step 602, a laser beam 104 is emitted onto at least one molecule 114 supported on a substrate 110.

At step 604, a spatial relationship between the laser beam 104 and the substrate 110 is spatially modulated at an identified frequency to cause the Raman light to be emitted 116 from the at least one molecule at the identified frequency. As discussed above, the spatial relationship may be modulated by modulating the laser beam 104 and/or the substrate 110 through use of any of a number of different types of modulating elements 130. As also discussed above, the spatial modulation may cause the laser beam 104 to irradiate one or more molecules during the modulation.

At step 606, the Raman light emitted 116 from the at least one molecule 114 is detected through operation of, for instance, the optical element(s) 118 and the detector(s) 120. As discussed above, the detector(s) 120 may comprise an array of detectors 402 configured to detect Raman light emitted 116 from molecules 114 located in multiple locations on the substrate 110.

At step 608, the detected Raman light emission(s) 116 are processed at the identified frequency to detect the molecule(s) 114. More particularly, for instance, a lock-in detection technique may be implemented on the detected Raman light emission(s) 116 at the identified frequency to thus enable the post-signal processing unit 124 to sample only the signal component ascribable to the molecule(s) 114.

Figure 7:
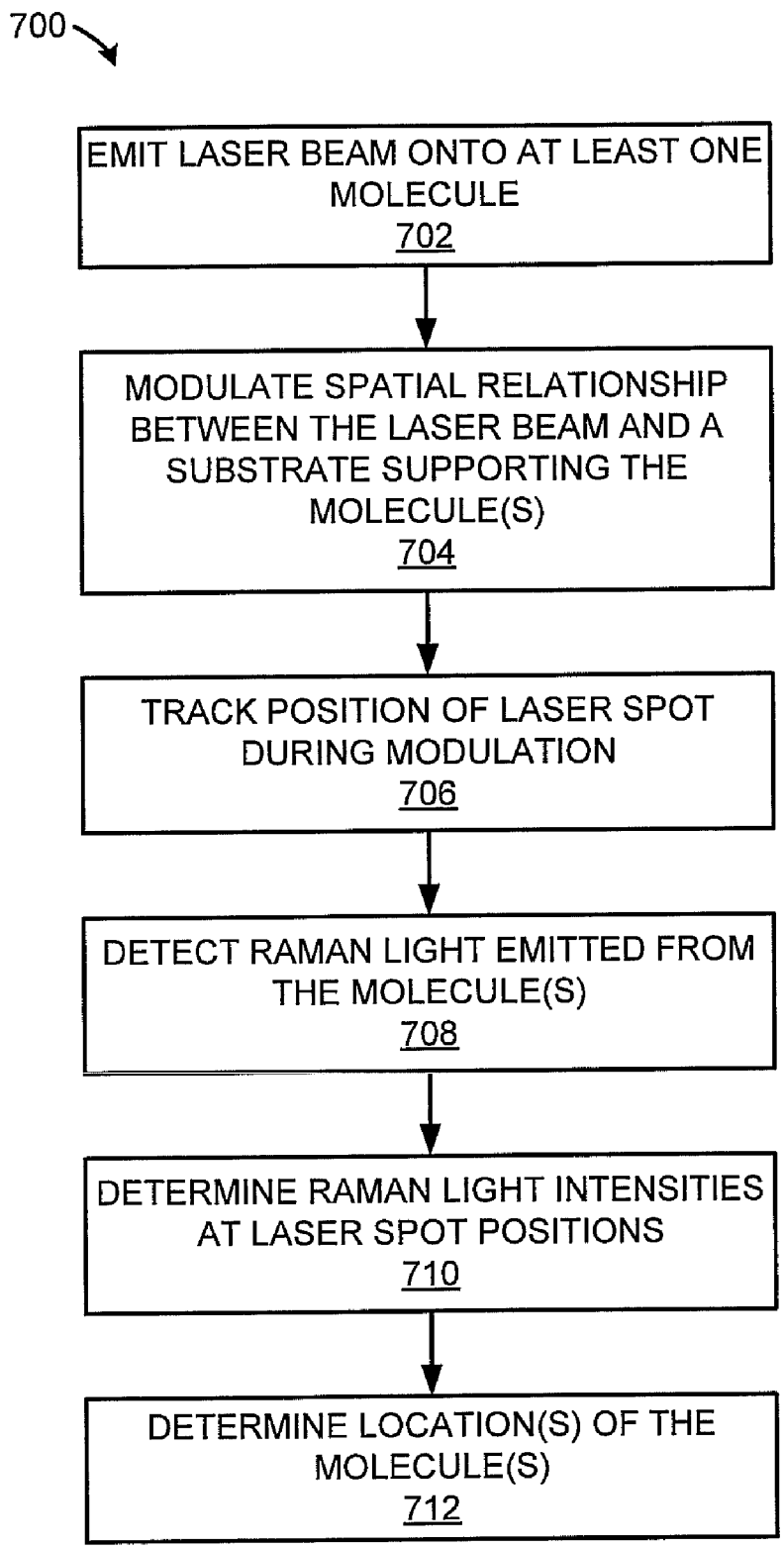
FIG. 7 shows a flow diagram of a method for detecting a location of at least one molecule with respect to a substrate through Raman light detection, according to an embodiment of the invention.

With reference now to FIG. 7, there is shown a flow diagram of a method 700 for detecting a location of at least one molecule 114 with respect to a substrate 110 through Raman light detection, according to an embodiment. It should be understood that the method 700 depicted in FIG. 7 may include additional steps and that some of the steps described herein may be removed and/or modified without departing from a scope of the method 700.

At step 702, a laser beam 104 is emitted onto at least one molecule 114 supported on a substrate 110.

At step 704, a spatial relationship between the laser beam 104 and the substrate 110 is modulated to cause a laser spot 108 of the laser beam 104 to modulate with respect to a position of the at least one molecule. The spatial relationship may be modulated by the modulating element 130 as discussed above.

At step 706, a position of the laser spot 108 with respect to the substrate 110 is tracked during the spatial relationship modulation. The position of the laser spot 108 with respect to the substrate 110 may be tracked through use of any suitable tracking implementation. For example, in instances where the position of the laser beam 104 is modulated, the settings of one or more optical devices that affect the location of the laser spot 108 may be tracked. As another example, in instances where the position of the substrate 110 is modulated, an encoder may be used to track to the position of the substrate 110.

At step 708, the Raman light emitted 116 from the at least one molecule 114 is detected through operation of, for instance, the optical element(s) 118 and the detector(s) 120. As discussed above, the detector(s) 120 may comprise an array of detectors 402 configured to detect Raman light emitted 116 from molecules 114 located in multiple locations on the substrate 110.

At step 710, the intensities of the Raman light 116 emitted at the different laser spot 108 positions with respect to the substrate 110 are determined, for instance, by the post-signal processing unit 114 or another computing device.

At step 712, the location(s) of the at molecule(s) are determined based upon the determined intensities and the laser spot 108 positions. More particularly, for instance, a Gaussian profile 510 (FIG. 5) correlating the intensities of the emitted Raman light 116 with respect to different locations on the substrate 110 may be generated. In addition, a peak intensity location 520 along the Gaussian profile 510 may be identified and the position on the substrate 110 corresponding to the peak intensity location 520 may be determined as the location of the molecule(s) 114.

Figure 8:
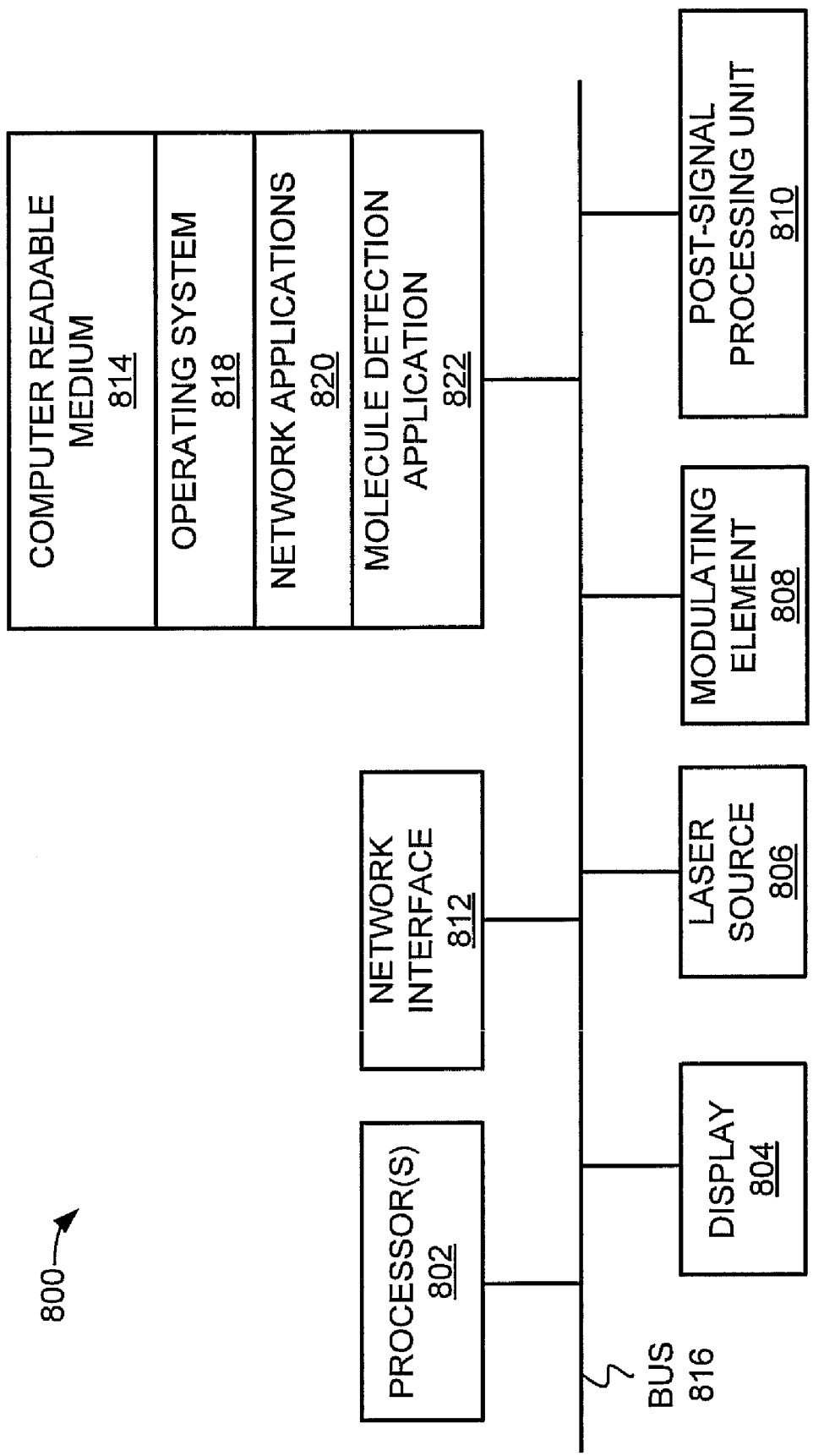
FIG. 8 shows a schematic representation of a computing device configured in accordance with embodiments of the present invention.

The methods 600 and 700 employed to detect at least one molecule 114 and to detect a location of at least one molecule 114 with respect to a substrate 110 may be implemented by a computing device, which may be a desktop computer, laptop, server, etc. Turning now to FIG. 8, there is shown a schematic representation of a computing device 800 configured in accordance with embodiments of the present invention. The device 800 includes one or more processors 802, such as a central processing unit; one or more display devices 804, such as a monitor; a laser source interface 806; a modulating element interface 808; a post-signal processing unit interface 810; one or more network interfaces 812, such as a Local Area Network LAN, a wireless 802.11x LAN, a 3G mobile WAN or a WiMax WAN; and one or more computer-readable mediums 814. Each of these components is operatively coupled to one or more buses 816. For example, the bus 816 may be an EISA, a PCI, a USB, a FireWire, a NuBus, or a PDS.

The computer readable medium 814 may be any suitable medium that participates in providing instructions to the processor 802 for execution. For example, the computer readable medium 810 can be non-volatile media, such as an optical or a magnetic disk; volatile media, such as memory; and transmission media, such as coaxial cables, copper wire, and fiber optics. Transmission media can also take the form of acoustic, light, or radio frequency waves.

The computer-readable medium 810 may also store an operating system 818, such as Mac OS, MS Windows, Unix, or Linux; network applications 820; and a molecule detection application 822. The operating system 818 may be multi-user, multiprocessing, multitasking, multithreading, real-time and the like. The operating system 818 may also perform basic tasks such as recognizing input from input devices, such as a keyboard or a keypad; sending output to the display 804, the laser source 102, the modulating element 130, and the post-signal processing unit 124; keeping track of files and directories on medium 814; controlling peripheral devices, such as disk drives, printers, image capture device; and managing traffic on the one or more buses 816. The network applications 820 include various components for establishing and maintaining network connections, such as software for implementing communication protocols including TCP/IP, HTTP, Ethernet, USB, and FireWire.

The molecule detection application 822 provides various software components for detecting molecules 114 and locations of molecules 114, as described above. In certain embodiments, some or all of the processes performed by the molecule detection application 822 may be integrated into the operating system 818. In certain embodiments, the processes can be at least partially implemented in digital electronic circuitry, or in computer hardware, firmware, software, or in any combination thereof.

What has been described and illustrated herein is an embodiment along with some of its variations. The terms, descriptions and figures used herein are set forth by way of illustration only and are not meant as limitations. Those skilled in the art will recognize that many variations are possible within the spirit and scope of the subject matter, which is intended to be defined by the following claims—and their equivalents—in which all terms are meant in their broadest reasonable sense unless otherwise indicated.

What is claimed is:

1. A apparatus for detecting at least one molecule using Raman light detection, said apparatus comprising:
   a substrate for supporting a sample containing the at least one molecule;
   a laser source for emitting a laser beam to cause Raman light emission from the at least one molecule;
   a modulating element for modulating a spatial relationship between the laser beam and the substrate at an identified frequency to cause the Raman light to be emitted from the at least one molecule at the identified frequency;
   at least one detector for detecting the Raman light emitted from the at least one molecule; and
   a post-signal processing unit configured to process the detected Raman light emission at the identified frequency to detect the at least one molecule.

2. The apparatus according to claim 1, wherein the modulating element is configured to modulate the spatial position of the laser beam with respect to the substrate at the identified frequency.

3. The apparatus according to claim 2, wherein the laser beam is configured to be transmitted through an optical waveguide, and wherein the modulating element comprises a mechanical device configured to modulate the position of the optical waveguide at the identified frequency along one or more dimensions.

4. The apparatus according to claim 2, wherein the modulating element comprises an electro-optic deflector configured to modulate the spatial position of the laser beam at the identified frequency along one or more dimensions.

5. The apparatus according to claim 2, wherein the sample comprises a first molecule at a first location of the substrate and a second molecule at a second location of the substrate, wherein the modulating element is configured to modulate the spatial position of the laser beam between the first location of the substrate and the second location of the substrate to cause Raman light to be cyclically emitted from the first molecule and the second molecule at the identified frequency, and wherein the post-signal processing unit is configured to process the Raman light emissions at the identified frequency for each of the first molecule and the second molecule.

6. The apparatus according to claim 1, wherein the modulating element is configured to modulate the spatial position of the substrate with respect to the laser beam along one or more dimensions.

7. The apparatus according to claim 6, wherein the sample comprises a first molecule at a first location of the substrate and a second molecule at a second location of the substrate, wherein the modulating element is configured to modulate the spatial position of the substrate to cause the laser beam to cyclically cause Raman light emission to occur from the first molecule and the second molecule at the identified frequency, and wherein the post-signal processing unit is configured to process the Raman light emissions at the identified frequency for each of the first molecule and the second molecule.

8. The apparatus according to claim 6, wherein the modulating element is configured to modulate the spatial position of the substrate by rotating the substrate at the identified frequency.

9. The apparatus according to claim 8, wherein the sample comprises a plurality of molecules positioned in a circular arrangement along the substrate, wherein the modulating element is configured to modulate the spatial position of the substrate to cause the laser beam to cyclically cause Raman light emission to occur from the plurality of molecules at the identified frequency, and wherein the post-signal processing unit is configured to process the Raman light emissions at the identified frequency for the plurality of molecules.

10. The apparatus according to claim 1, further comprising:
an array of detectors configured to detect Raman light emissions from a plurality of molecules; and
wherein the post-signal processing unit is configured to process each of the detected Raman light emissions at the identified frequency.

11. The apparatus according to claim 1, wherein the post-signal processing unit is further configured to determine a location of the at least one molecule on the substrate based upon intensities of the detected Raman light emissions at a plurality of spatial relationships between the laser beam and the substrate.

12. A method for detecting at least one molecule supported on a substrate through Raman light detection, said method comprising:
is emitting a laser beam onto the at least one molecule to cause emission of Raman light from the at least one molecule;
modulating a spatial relationship between the laser beam and the substrate at an identified frequency to cause the Raman light to be emitted from the at least one molecule at the identified frequency;
detecting the Raman light emitted from the at least one molecule; and
processing the detected Raman light emission at the identified frequency to detect the at least one molecule.

13. The method according to claim 12, wherein modulating the spatial relationship between the laser beam and the substrate further comprises modulating the spatial position of the laser beam with respect to the substrate along one or more dimensions.

14. The method according to claim 13, wherein modulating the spatial position of the laser beam further comprises modulating the spatial position of the laser beam to cause the laser beam to modulate between irradiating a first molecule and a second molecule at the identified frequency,
wherein detecting the Raman light emitted from the at least one molecule further comprises detecting Raman light emitted from the first molecule and the second molecule; and
wherein processing the detected Raman light emission further comprises processing the detected Raman light emissions at the identified frequency for each of the first molecule and the second molecule.

15. The method according to claim 12, wherein modulating the spatial relationship between the laser beam and the substrate further comprises modulating the spatial position of the substrate with respect to the laser beam along one or more dimensions.

16. The method according to claim 15, wherein modulating the spatial position of the substrate further comprises modulating the spatial position of the is substrate to cause the laser beam to irradiate the first molecule on the second molecule at the identified frequency,
wherein detecting the Raman light emitted from the at least one molecule further comprises detecting Raman light cyclically emitted from the first molecule and the second molecule; and
wherein processing the detected Raman light emission further comprises processing the detected Raman light emissions at the identified frequency for each of the first molecule and the second molecule.

17. The method according to claim 15, wherein modulating the spatial position of the substrate further comprises rotating the substrate at the identified frequency.

18. The method according to claim 12, further comprising:
determining intensities of the Raman light emissions at a plurality of respective spatial positions of the laser beam and the substrate; and
determining a location of the least one molecule on the substrate based upon the determined intensities.

19. A method for detecting a location of at least one molecule with respect to a substrate through Raman light detection, said method comprising:
emitting a laser beam onto the at least one molecule to cause emission of Raman light from the at least one molecule;
modulating a spatial relationship between the laser beam and the substrate to cause a laser spot of the laser beam to modulate with respect to a position of the at least one molecule;
tracking a position of the laser spot with respect to the substrate during to the spatial relationship modulation;
detecting the Raman light emitted from the at least one molecule;
determining intensities of the Raman light emitted from the at least one molecule at different laser spot positions with respect to the substrate; and
determining the location of the at least one molecule based upon the determined intensities and the laser spot positions.

20. The method according to claim 19, wherein determining the location of the at least one molecule further comprises determining the location of the at least one molecule to correspond to the laser spot position having the substantially highest Raman light intensity.

* * * * *

UNITED STATES PATENT AND TRADEMARK OFFICE
CERTIFICATE OF CORRECTION

| | | |
|---|---|---|
| PATENT NO. | : 8,208,137 B2 | |
| APPLICATION NO. | : 12/696853 | |
| DATED | : June 26, 2012 | |
| INVENTOR(S) | : Min Hu et al. | |

It is certified that error appears in the above-identified patent and that said Letters Patent is hereby corrected as shown below:

In column 9, line 28, in Claim 12, before "emitting" delete "is".

In column 10, line 9, in Claim 16, after "of the" delete "is".

In column 10, line 27, in Claim 18, after "of the" insert -- at --.

In column 10, line 39, in Claim 19, after "during" delete "to".

Signed and Sealed this
Eighth Day of January, 2013

David J. Kappos
*Director of the United States Patent and Trademark Office*